US008755585B2

(12) United States Patent
Nakanishi et al.

(10) Patent No.: US 8,755,585 B2
(45) Date of Patent: Jun. 17, 2014

(54) X-RAY COMPUTED TOMOGRAPHY APPARATUS

(75) Inventors: Satoru Nakanishi, Utsunomiya (JP);
Yasuhiro Noshi, Otawara (JP)

(73) Assignees: Kabushiki Kaisha Toshiba, Tokyo (JP);
Toshiba Medical Systems Corporation,
Otawara-shi (JP)

( * ) Notice: Subject to any disclaimer, the term of this patent is extended or adjusted under 35 U.S.C. 154(b) by 105 days.

(21) Appl. No.: 13/107,368

(22) Filed: May 13, 2011

(65) Prior Publication Data

US 2011/0280459 A1    Nov. 17, 2011

(30) Foreign Application Priority Data

May 17, 2010    (JP) ................................. 2010-113521

(51) Int. Cl.
*G06K 9/00*    (2006.01)
(52) U.S. Cl.
USPC ........................................................ 382/131
(58) Field of Classification Search
None
See application file for complete search history.

(56) References Cited

U.S. PATENT DOCUMENTS

| 7,181,084 B2* | 2/2007 | Jostschulte ................... 382/260 |
| 2003/0086105 A1* | 5/2003 | Jostschulte ................... 358/1.9 |
| 2003/0099323 A1* | 5/2003 | Nagata et al. ..................... 378/4 |
| 2009/0161935 A1* | 6/2009 | Bruder et al. ................. 382/131 |
| 2011/0052030 A1* | 3/2011 | Bruder et al. ................. 382/131 |
| 2011/0142314 A1* | 6/2011 | Hsieh et al. ................... 382/131 |
| 2011/0150305 A1* | 6/2011 | Zeng et al. .................... 382/131 |

FOREIGN PATENT DOCUMENTS

| JP | 1-237887 | 9/1989 |
| JP | 2007-14755 | 1/2007 |

OTHER PUBLICATIONS

Seperate CT Reconstruction for 3D wavelet based noise reduction using correlation analysis (Bordsdorf et al, IEEE Mar. 2007.*
Office Action mailed Jan. 7, 2014, in Japanese Patent Application No. 2010-113521 (with English-language Translation).

* cited by examiner

*Primary Examiner* — Nancy Bitar
(74) *Attorney, Agent, or Firm* — Oblon, Spivak, McClelland, Maier & Neustadt, L.L.P.

(57) ABSTRACT

According to one embodiment, an X-ray computed tomography apparatus includes an X-ray tube, an X-ray detector, and a rotating unit. The first reconstruction processing reconstructs a clinical image based on projection data detected by the X-ray detector. The second reconstruction processing reconstructs a noise image based on noise data. The clinical image is combined with the noise image.

9 Claims, 4 Drawing Sheets

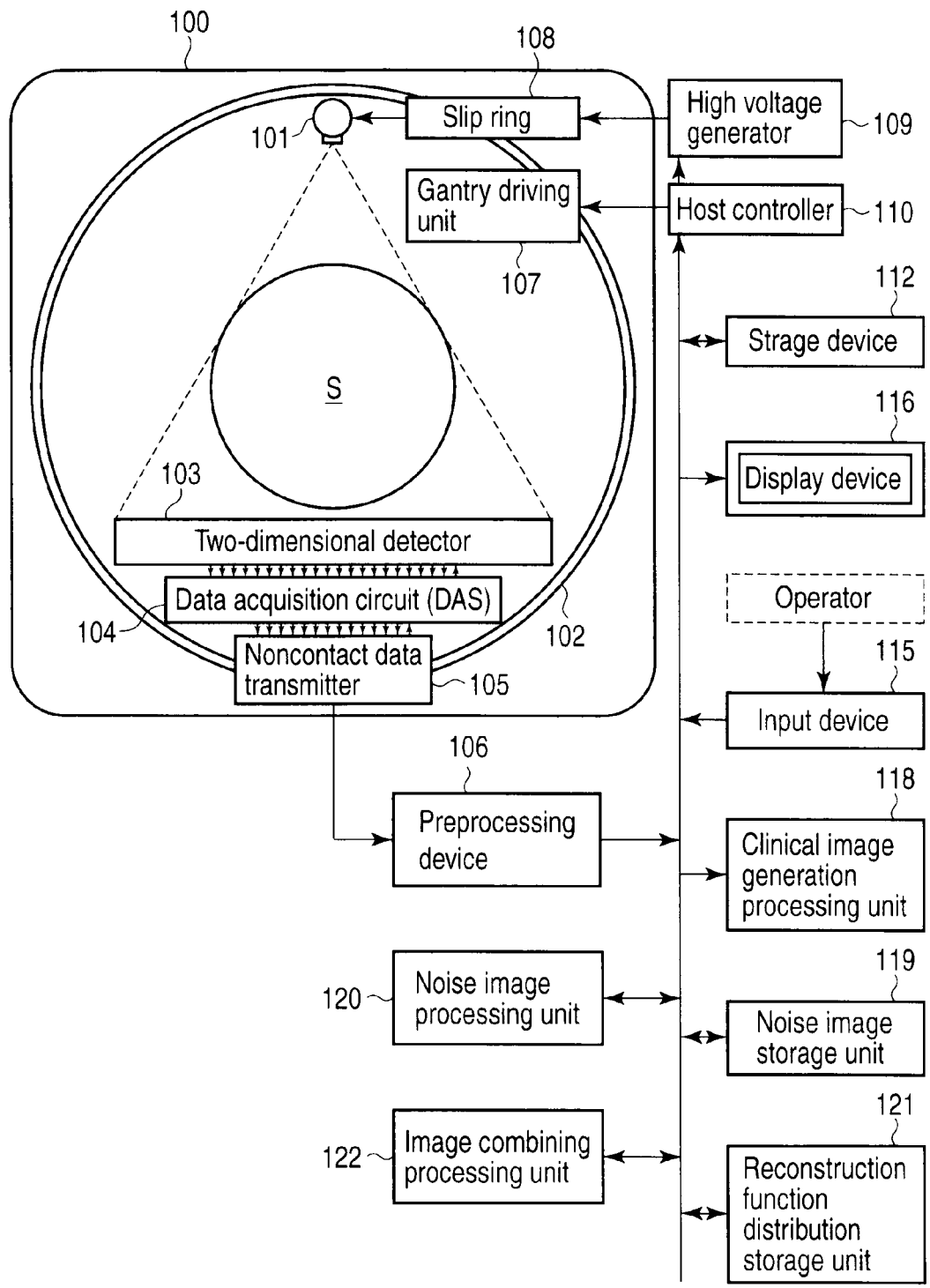
F I G. 1

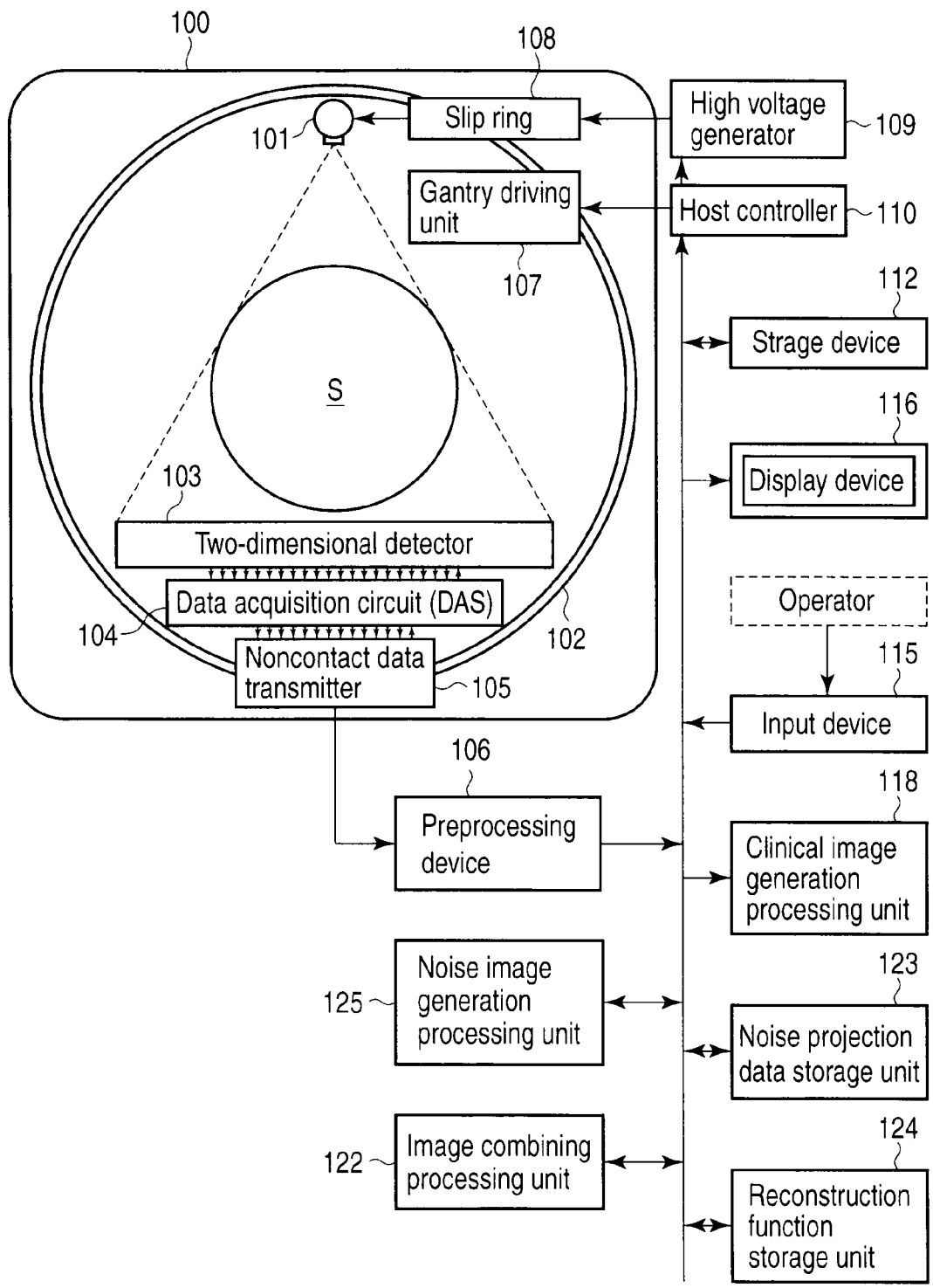
F I G. 3

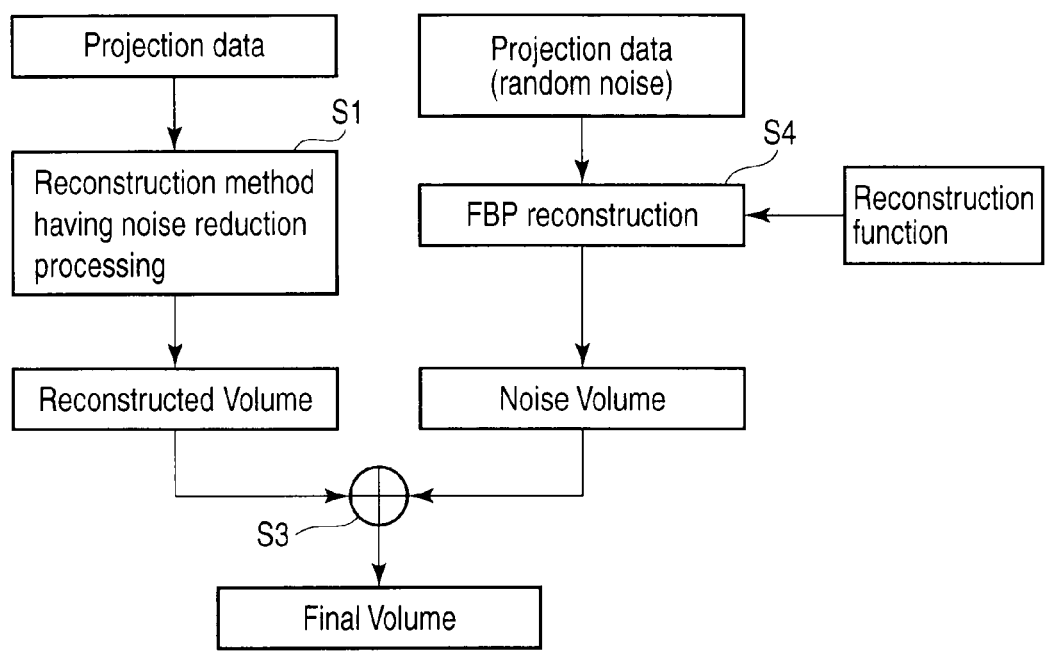
F I G. 4

X-RAY COMPUTED TOMOGRAPHY APPARATUS

CROSS-REFERENCE TO RELATED APPLICATIONS

This application is based upon and claims the benefit of priority from Japanese Patent Application No. 2010-113521, filed May 17, 2010; the entire contents of which are incorporated herein by reference.

FIELD

Embodiments described herein relate generally to an X-ray computed tomography apparatus.

BACKGROUND

Image noise reduction processing changes the granularity of image noise. Noise reduction processing is effective for the image reconstructed by iterative approximation processing. On the other hand, the granularity greatly deteriorates. Many observers have long experience in observing images having certain granularities.

The prior art includes a method of combining a "reconstructed image having undergone noise reduction by iterative approximation processing" with an "original image". Combining the original image will add granularity components to the image having undergone noise reduction processing, thereby minimizing a sense of discomfort in appearance.

A problem of this technique is that the artifact components of the original image are also added to the reconstructed image to result in a reduction in image improving effect. When obtaining granularity like that of an image reconstructed by filtered back projection processing (to be referred to as an FBP image hereinafter) from a "reconstructed image having undergone noise reduction by iterative approximation processing", if the input source data is minority data, a deterioration in image quality becomes noticeable because aliasing artifact is noticeable in FBP reconstruction for the reconstruction of an original image.

Another problem in the prior art is that although FBP reconstruction can control granularity by controlling the frequency characteristics of a ramp filter called a reconstruction function, it is theoretically difficult to provide a unit for operating granularity for an image reconstructed by iterative approximation processing. This makes it difficult to obtain granularity in accordance with the preferences of customers.

BRIEF DESCRIPTION OF THE DRAWINGS

FIG. 1 is a view showing the arrangement of an X-ray computed tomography apparatus according to the first embodiment;

FIG. 3 is a view showing the arrangement of an X-ray computed tomography apparatus according to the second embodiment; and FIG. 4 is a flowchart showing a procedure for generating a final image (volume) according to the second embodiment.

DETAILED DESCRIPTION

Figure 2:
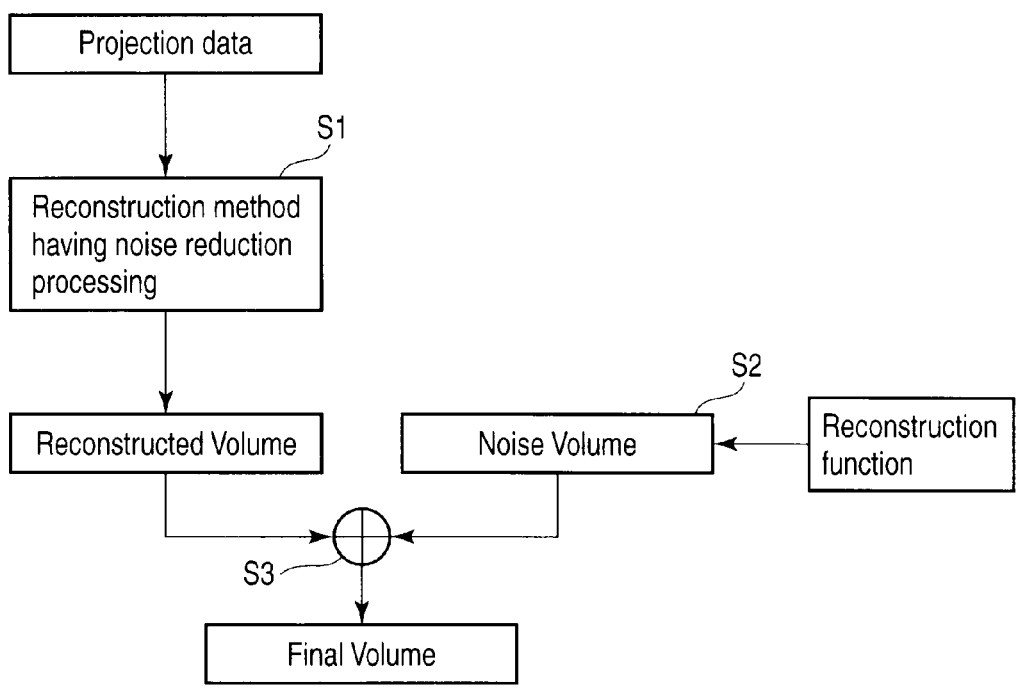
FIG. 2 is a flowchart showing a procedure for generating a final image (volume) according to the first embodiment.

In general, according to one embodiment, an X-ray computed tomography apparatus includes an X-ray tube, an X-ray detector, and a rotating unit. The first reconstruction processing reconstructs a clinical image based on projection data detected by the X-ray detector. The second reconstruction processing reconstructs a noise image based on noise data stored in advance. The clinical image is combined with the noise image and displayed (frame addition processing).

The X-ray computed tomography apparatus according to this embodiment will be described below with reference to the views of the accompanying drawing.

First of all, a basic feature of this embodiment is to provide granularity for a clinical image by combining a "reconstructed image (clinical image) having undergone noise reduction by iterative approximation processing" with an "image (noise image) having noise components". A "noise image" to be combined with a clinical image is stored upon being reconstructed in advance by filtered back projection processing using a specific reconstruction function or another type of analytical reconstruction processing from projection data (e.g., projection data associated with uniform noise) associated with a plurality of views having only noise components (first embodiment). Alternatively, it is possible to individually reconstruct a "noise image" to be combined with a clinical image by storing projection data associated with a plurality of views having only noise components in advance and performing filtered back projection processing using a reconstruction function arbitrarily selected by the operator or another type of analytical reconstruction processing at the same resolution as that set in scanning for the acquisition of projection data associated with an object which are used for clinical image reconstruction (second embodiment).

Note that X-ray computed tomography apparatuses include a rotate/rotate-type apparatus in which an X-ray tube and a radiation detector rotate together around an object to be examined and a stationary/rotate-type apparatus in which many detection elements are arrayed in the form of a ring, and only an X-ray tube rotates around an object. This embodiment can be applied to either type. In this case, the rotate/rotate type, which is currently the mainstream, will be exemplified. In order to reconstruct one-slice tomogram data, projection data corresponding to one rotation around an object, i.e., about 360°, is required, or 180°±α (α: fan angle) projection data is required in the half scan method. The embodiment can be applied to either of these reconstruction schemes. As units of converting incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor by X-rays and migration of the electron-hole pairs to an electrode, i.e., a photoconductive phenomenon. As an X-ray detection element, either of these schemes can be used. In this case, the former type, i.e., the indirect conversion type, will be exemplified. Recently, with advances toward the commercialization of a so-called multi-tube type X-ray computed tomography apparatus having a plurality of pairs of X-ray tubes and X-ray detectors mounted on a rotating ring, related techniques have been developed. The embodiment can be applied to both a conventional single-tube type X-ray computed tomography apparatus and a multi-tube type X-ray computed tomography apparatus. The single-tube type X-ray computed tomography apparatus will be exemplified here.

FIG. 1 shows the arrangement of the X-ray computed tomography apparatus according to the first embodiment. The X-ray computed tomography apparatus according to the first embodiment includes a host controller 110 as a main control unit and a gantry 100. An opening portion is formed in the central portion of the gantry 100. An object is placed on the top of a bed (not shown) and inserted into the opening portion. The gantry 100 includes an X-ray tube 101 and an X-ray detector 103. As the X-ray tube 101, an X-ray tube of a type that generates an X-ray cone beam is used in accordance with cone beam scanning. As the X-ray detector 103, a multi-slice type or two-dimensional array type detector having X-ray detection elements arrayed two-dimensionally is used. The X-ray detector 103 is mounted on a ring-like rotating frame 102 which is rotated by a gantry driving unit 107, together with the X-ray tube 101.

A high voltage generator 109 applies a tube voltage (high voltage) between the cathode and anode of the X-ray tube 101 through a slip ring 108. The high voltage generator 109 also supplies a filament current to the filament of the X-ray tube 101. The application of a tube voltage and the supply of a filament current will generate X-rays The X-ray detector 103 includes a plurality of X-ray detection elements each having, for example, a 0.5 mm×0.5 mm square light-receiving surface. For example, 916 X-ray detection elements are arrayed in an arcuated form along the channel direction. For example, 64 detection element rows are arranged parallel in the slice direction.

A data acquisition circuit 104 generally called a DAS (Data Acquisition System) converts a signal output from the X-ray detector 103 for each channel into a voltage signal, amplifies it, and further converts it into a digital signal. This data (to be also referred to as raw data) is sent to a preprocessing device 106 via a noncontact data transmitter 105 using magnetism or light as a medium. The preprocessing device 106 performs correction processing such as sensitivity correction for the raw data. The preprocessed raw data is generally called projection data. A projection data storage unit 112 stores each projection data in association with a view angle representing the rotational angle of the X-ray tube 101, a channel number, a column number, and a code representing the position of the top. Note that the projection data actually acquired by scanning an object will be referred to as clinical projection data to discriminate it from projection data associated with only noise components (to be described later). In addition, projection data associated with only noise components will be referred to as noise projection data.

A clinical image generation processing unit 118 generates clinical image data based on clinical projection data. Clinical image data is a secondary original image (slice image) or a tertiary original image (volume). Clinical image data is a low-noise image, as indicated by "S1" in FIG. 2. Image generation processing performed by the clinical image generation processing unit 118 typically corresponds to ART (Arithmetic Reconstruction Processing), a MAP-EM method, or another type of iterative approximation processing. Image reconstruction processing may be processing corresponding to filtered back projection processing, a convolution integral method, a Fourier transform method, or another analytical reconstruction method. When using processing corresponding to filtered back projection processing or another analytical reconstruction method, noise reduction filtering processing is combined with processing corresponding to this analytical reconstruction method. This generates a low-noise clinical image. A typical example of noise reduction filtering processing is spatial smoothing processing.

A noise image storage unit 119 stores the data of a noise image representing granularity higher than that of a clinical image. A noise image is reconstructed in advance with a specific spatial resolution (a specific pixel size) by filtered back projection processing or another type of analytical reconstruction processing using a specific reconstruction function based on projection data associated with a plurality of views having only noise components obtained by scanning, for example, a phantom made of a homogeneous material. The noise image storage unit 119 then stores the noise image. A noise component is defined by Gaussian noise with an average value of 0 and a standard deviation $\sigma$.

A noise image processing unit 120 applies enlargement/reduction processing, convolution processing (S2 in FIG. 2), and spatial smoothing processing to a noise image. Enlargement/reduction processing is processing for equalizing the spatial resolution (pixel size) of the noise image to the spatial resolution (pixel size) of the clinical image.

Convolution processing is convolution of a spatial distribution corresponding to a reconstruction function in a real space or frequency space for a noise image. The spatial distribution corresponding to the reconstruction function is a granularity distribution obtained by reconstructing uniform projection data by processing corresponding to filtered back projection processing. A plurality of granularity distributions are generated in advance by using a plurality of kinds of reconstruction functions and stored in a reconstruction function distribution storage unit 121. The operator can arbitrarily select a granularity distribution via an input device 115. Selecting a granularity distribution makes it possible to arbitrarily control the granularity of a noise image.

Adjusting a smoothing coefficient for smoothing processing can arbitrarily control noise intensity. When adjusting a smoothing coefficient, the operator may arbitrarily select or designate a smoothing coefficient via the input device 115. Alternatively, it is possible to estimate the intensity of image noise from a clinical image, typically calculate a standard deviation, and select one of smoothing coefficients, associated with standard deviations in advance, in accordance with the calculated standard deviation.

An image combining processing unit 122 combines a low-noise clinical image with a noise image having undergone image processing by a noise image processing unit 120 (S3 in FIG. 2), thereby obtaining a final image with granularity being added to the clinical image. This combining processing is typically weighted addition of pixels. A uniform weight may be provided for an entire image area. Alternatively, it is possible to decrease the weight for a noise image with respect to an edge portion (an area where the spatial frequency is relatively high) of a region of a clinical image so as to relatively increase the contribution ratio of the clinical image and suppress noise. In contrast, it is possible to increase the weight for the noise image with respect to a uniform portion (an area where the spatial frequency is relatively low) exhibiting small changes in the luminance of the clinical image so as to decrease the contribution ratio of the clinical image and enhance noise. A display device 116 displays the final image.

As described above, it is possible to provide granularity for a clinical image by combining a "reconstructed image (clinical image) having undergone noise reduction by iterative approximation processing or the like" with an "image (noise image) having noise components". In addition, selecting a granularity distribution can arbitrarily adjust the degree of granularity.

FIG. 3 shows the arrangement of an X-ray computed tomography apparatus according to the second embodiment. The same reference numerals as in FIG. 3 denote the same parts in FIG. 1, and a description of them will be omitted.

In the first embodiment described above, a noise image prepared in advance is properly processed and combined with a clinical image. In the second embodiment, projection data (to be referred to as noise projection data) covering a plurality of views having only noise components is prepared in advance. A noise image is then reconstructed from this noise projection data by filtered back projection processing, a convolution integral method, a Fourier transform method, or another analytical reconstruction method, and combined with a clinical image.

A noise projection data storage unit 123 stores projection data noise projection data associated with a plurality of views having only noise components. This noise projection data is formed by a Gaussian noise model with an average value of 0 and a standard deviation σ or another kind of noise model. Alternatively, noise projection data is obtained by scanning, for example, a phantom made of a homogenous material. The format of this noise projection data may differ from that of real projection data. For example, if the data count of projection data actually acquired from an object is 100 views/rotation, the data count of noise projection data may be 100 views/rotation or less, e.g., 80 views/rotation, or more, e.g., 120 views/rotation. Typically, the data count of noise projection data is preferably equal or approximate to that of projection data actually acquired from an object so as not to increase the sense of discomfort of granularity.

A noise image generation processing unit 125 generates a noise image by processing corresponding to processing corresponding to filtered back projection processing, a convolution integral method, a Fourier transform method, or another analytical reconstruction method using an arbitrary reconstruction function based on noise projection data (S4 in FIG. 4). A noise image is reconstructed in advance at the same spatial resolution (pixel size) as that in reconstruction processing of a clinical image. The operator arbitrarily selects a reconstruction function used by the noise image generation processing unit 125 from a plurality of reconstruction functions stored in a reconstruction function storage unit 124 via an input device 115. Selecting this reconstruction function makes it possible to arbitrarily adjust the granularity of a noise image. The reconstruction function to be selected should typically differ from the reconstruction function used by a clinical image generation processing unit 118 when it uses an analytical reconstruction method.

An image combining processing unit 122 can obtain a final image with granularity being added to a low-noise clinical image by combining the clinical image with the noise image generated by the noise image generation processing unit 125.

As described above, it is possible to provide granularity for a clinical image by combining a "reconstructed image (clinical image) having undergone noise reduction by iterative approximation processing or the like" with an "image (noise image) having noise components", and to arbitrarily adjust the degree of granularity by selecting a reconstruction function used in noise image reconstruction.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography apparatus, comprising:
an X-ray tube configured to generate an X-ray;
an X-ray detector configured to generate projection data by detecting the X-ray transmitted through an object;
a rotating unit configured to rotatably support both the X-ray tube and the X-ray detector around the object;
a first reconstruction processing unit configured to reconstruct a clinical image by performing first reconstruction processing based on the generated projection data;
a second reconstruction processing unit configured to reconstruct a noise image by performing second reconstruction processing different from the first reconstruction processing based on noise data; and
an image combining processing unit configured to combine the clinical image with the noise image,
wherein noise reduction effect of the second reconstruction processing is smaller than that of the first reconstruction processing, and image granularity of the second reconstruction processing is greater than that of the first reconstruction processing, and
the second reconstruction processing unit is configured to reconstruct the noise image based on the noise data, which comprises projection data associated with a plurality of views having only noise components and obtained by scanning.

2. The apparatus of claim 1, wherein the second reconstruction processing comprises one of filtered back projection processing and another type of analytical reconstruction processing.

3. The apparatus of claim 2, wherein the second reconstruction processing comprises a reconstruction function selected from a plurality of reconstruction functions in accordance with an operator instruction.

4. The apparatus of claim 1, wherein the first reconstruction processing comprises one of ART processing and another type of iterative approximation processing.

5. The apparatus of claim 1, wherein the first reconstruction processing comprises ART processing, and the second reconstruction processing comprises filtered back projection processing.

6. The apparatus of claim 1, wherein the first reconstruction processing reduces noise of the clinical image.

7. The apparatus of claim 1, wherein the second reconstruction processing unit is configured to reconstruct the noise image based on the noise data, which corresponds to Gaussian noise with an average value of 0 and a standard deviation σ.

8. The apparatus of claim 1, wherein the first reconstruction processing unit is configured to reconstruct the clinical image so that the clinical image comprises volume data, and the second reconstruction unit is configured to reconstruct the noise image so that the noise image comprises volume data.

9. The apparatus of claim 1, further comprising a noise image processing unit configured to apply enlargement/reduction processing to the noise image in accordance with a pixel size of the clinical image and convolute one of a real spatial distribution and a frequency spatial distribution corresponding to an arbitrary reconstruction function with respect to a noise image to which the enlargement/reduction processing is applied.

* * * * *